(12) United States Patent
Stokes et al.

(10) Patent No.: US 7,615,060 B2
(45) Date of Patent: Nov. 10, 2009

(54) ENDOSCOPIC SUTURING DEVICE

(75) Inventors: Michael J. Stokes, Cincinnati, OH (US); Mark S. Ortiz, Milford, OH (US)

(73) Assignee: Ethicon-Endo Surgery, Inc., Cincinnati, OH (US)

( * ) Notice: Subject to any disclaimer, the term of this patent is extended or adjusted under 35 U.S.C. 154(b) by 732 days.

(21) Appl. No.: 11/150,481

(22) Filed: Jun. 13, 2005

(65) Prior Publication Data

US 2006/0282089 A1    Dec. 14, 2006

(51) Int. Cl.
*A61B 17/04* (2006.01)
(52) U.S. Cl. .................. 606/145; 606/139; 606/144
(58) Field of Classification Search .............. 606/139, 606/144, 145, 148, 147
See application file for complete search history.

(56) References Cited

U.S. PATENT DOCUMENTS

| | | | | |
|---|---|---|---|---|
| 1,822,330 A | * | 9/1931 | Ainslie | 606/145 |
| 4,345,601 A | * | 8/1982 | Fukuda | 606/147 |
| 4,458,403 A | * | 7/1984 | Foster | 29/434 |
| 4,557,265 A | * | 12/1985 | Andersson | 606/144 |
| 4,899,746 A | * | 2/1990 | Brunk | 606/144 |
| 5,080,663 A | | 1/1992 | Mills et al. | |
| 5,306,281 A | * | 4/1994 | Beurrier | 606/144 |
| 5,376,101 A | | 12/1994 | Green et al. | |
| 5,437,681 A | | 8/1995 | Meade et al. | |
| 5,462,558 A | | 10/1995 | Kolesa et al. | |
| 5,470,338 A | * | 11/1995 | Whitfield et al. | 606/144 |
| 5,474,568 A | * | 12/1995 | Scott | 606/144 |
| 5,514,159 A | | 5/1996 | Matula et al. | |
| 5,527,321 A | * | 6/1996 | Hinchliffe | 606/144 |
| 5,540,705 A | | 7/1996 | Meade et al. | |
| 5,571,119 A | | 11/1996 | Atala | |
| 5,586,986 A | * | 12/1996 | Hinchliffe | 606/147 |
| 5,709,693 A | * | 1/1998 | Taylor | 606/145 |
| 5,713,910 A | | 2/1998 | Gordon et al. | |
| 5,741,277 A | * | 4/1998 | Gordon et al. | 606/144 |
| 5,766,186 A | * | 6/1998 | Faraz et al. | 606/145 |
| 5,792,153 A | | 8/1998 | Swain et al. | |
| 5,814,071 A | | 9/1998 | McDevitt et al. | |
| 5,860,992 A | * | 1/1999 | Daniel et al. | 606/145 |
| 6,036,694 A | | 3/2000 | Goble et al. | |
| 6,238,336 B1 | | 5/2001 | Ouchi | |
| 6,346,111 B1 | | 2/2002 | Gordon et al. | |
| 6,352,503 B1 | | 3/2002 | Matsui et al. | |
| 6,406,424 B1 | * | 6/2002 | Williamson et al. | 600/201 |
| 6,443,962 B1 | * | 9/2002 | Gaber | 606/144 |
| 6,454,778 B2 | * | 9/2002 | Kortenbach | 606/144 |
| 6,494,888 B1 | | 12/2002 | Laufer et al. | |
| 6,506,196 B1 | | 1/2003 | Laufer | |

(Continued)

FOREIGN PATENT DOCUMENTS

EP    1545336    6/2005

(Continued)

*Primary Examiner*—Darwin P Erezo
(74) *Attorney, Agent, or Firm*—Welsh & Flaxman LLC (57) ABSTRACT

An endoscopic apparatus for the continuous application of a suture includes a suturing body that is shaped and dimensioned for attachment to the distal end of a commercially available endoscope in a manner permitting actuation thereof. The suturing body is composed of a suture housing in which a needle and drive assembly are housed for movement of the needle about a continuous circular path facilitating the application of a suture secured to a distal end of the needle. The drive assembly includes a rocker that moves along the suture housing under the control of a drive cable and a pin, wherein actuation of the drive cable and pin cause the rocker to selectively engage and disengage the needle causing the needle to move about a circular path in a continuous manner.

16 Claims, 5 Drawing Sheets

U.S. PATENT DOCUMENTS

| | | | |
|---|---|---|---|
| 6,551,329 B1* | 4/2003 | Kortenbach et al. | 606/144 |
| 6,558,400 B2 | 5/2003 | Deem et al. | |
| 6,656,194 B1 | 12/2003 | Gannoe et al. | |
| 6,663,639 B1 | 12/2003 | Laufer et al. | |
| 6,719,763 B2* | 4/2004 | Chung et al. | 606/144 |
| 6,719,764 B1 | 4/2004 | Gellman et al. | |
| 6,746,460 B2 | 6/2004 | Gannoe et al. | |
| 6,755,843 B2 | 6/2004 | Chung et al. | |
| 6,773,440 B2 | 8/2004 | Gannoe et al. | |
| 6,835,200 B2 | 12/2004 | Laufer et al. | |
| 6,908,427 B2 | 6/2005 | Fleener et al. | |
| 6,923,819 B2 | 8/2005 | Meade et al. | |
| 6,955,643 B2* | 10/2005 | Gellman et al. | 600/104 |
| 7,004,951 B2* | 2/2006 | Gibbens, III | 606/144 |
| 7,048,749 B2* | 5/2006 | Kortenbach et al. | 606/144 |
| 7,442,198 B2* | 10/2008 | Gellman et al. | 606/144 |
| 2002/0107530 A1 | 8/2002 | Sauer et al. | |
| 2002/0193809 A1 | 12/2002 | Meade et al. | |
| 2003/0083674 A1 | 5/2003 | Gibbens, III | |
| 2003/0171760 A1 | 9/2003 | Gambale | |
| 2003/0181924 A1 | 9/2003 | Yamamoto et al. | |
| 2003/0208209 A1* | 11/2003 | Gambale et al. | 606/144 |
| 2003/0233104 A1 | 12/2003 | Gellman et al. | |
| 2003/0233108 A1 | 12/2003 | Gellman et al. | |
| 2004/0034369 A1 | 2/2004 | Sauer et al. | |
| 2004/0044354 A1 | 3/2004 | Gannoe et al. | |
| 2004/0059350 A1 | 3/2004 | Gordon et al. | |
| 2004/0082963 A1 | 4/2004 | Gannoe et al. | |
| 2004/0088008 A1 | 5/2004 | Gannoe et al. | |
| 2004/0122473 A1 | 6/2004 | Ewers et al. | |
| 2004/0138682 A1 | 7/2004 | Onuki et al. | |
| 2004/0147941 A1 | 7/2004 | Takemoto et al. | |
| 2004/0147958 A1 | 7/2004 | Lam et al. | |
| 2004/0162568 A1 | 8/2004 | Saadat et al. | |
| 2004/0194790 A1 | 10/2004 | Laufer et al. | |
| 2004/0210243 A1 | 10/2004 | Gannoe et al. | |
| 2004/0260344 A1 | 12/2004 | Lyons et al. | |
| 2005/0015101 A1 | 1/2005 | Gibbens, III et al. | |
| 2005/0055038 A1* | 3/2005 | Kelleher et al. | 606/151 |
| 2005/0070931 A1 | 3/2005 | Li et al. | |
| 2005/0075653 A1 | 4/2005 | Saadat et al. | |
| 2006/0020167 A1 | 1/2006 | Sitzmann | |
| 2006/0069396 A1* | 3/2006 | Meade et al. | 606/144 |

FOREIGN PATENT DOCUMENTS

| | | |
|---|---|---|
| EP | 1569709 | 9/2005 |
| EP | 1582138 | 10/2005 |
| EP | 1584295 | 10/2005 |
| EP | 1586275 | 10/2005 |
| EP | 1639936 | 3/2006 |
| WO | WO97/29694 | 8/1997 |
| WO | WO99/12482 | 3/1999 |
| WO | WO99/47050 | 9/1999 |
| WO | WO00/61012 | 10/2000 |
| WO | WO01/10312 | 2/2001 |
| WO | WO01/66001 | 9/2001 |
| WO | WO02/35980 | 5/2002 |
| WO | WO03/090630 | 11/2003 |
| WO | WO2004/021894 | 3/2004 |

* cited by examiner

ENDOSCOPIC SUTURING DEVICE

BACKGROUND OF THE INVENTION

1. Field of the Invention

The present invention relates to laparoscopic surgical instruments. More particularly, the invention relates to an endoscopic suturing device for continuous suture application.

2. Description of the Prior Art

Endoscopic procedures have been rapidly developing over the past decade. These procedures often allow for the performance of surgical procedures with minimal trauma when compared to prior techniques requiring large external opening to expose the internal organ or tissue requiring repair.

In addition to the many areas in which endoscopic procedures have found use, endoscopic procedures have been developed for surgical procedures addressing morbid obesity. Morbid obesity is a serious medical condition. In fact, morbid obesity has become highly pervasive in the United States, as well as other countries, and the trend appears to be heading in a negative direction. Complications associated with morbid obesity include hypertension, diabetes, coronary artery disease, stroke, congestive heart failure, multiple orthopedic problems and pulmonary insufficiency with markedly decreased life expectancy. With this in mind, and as those skilled in the art will certainly appreciate, the monetary and physical costs associated with morbid obesity are substantial. In fact, it is estimated the costs relating to obesity are in excess of 100 billion dollars in the United States alone.

A variety of surgical procedures have been developed to treat obesity. One procedure is Roux-en-Y gastric bypass (RYGB). This operation is highly complex and is commonly utilized to treat people exhibiting morbid obesity. Around 35,000 procedures are performed annually in the United States alone. Other forms of bariatric surgery include Fobi pouch, bilio-pancreatic diversion, and gastroplasty or "stomach stapling". In addition, implantable devices are known which limit the passage of food through the stomach and affect satiety.

RYGB involves movement of the jejunum to a high position using a Roux-en-Y loop. The stomach is completely divided into two unequal portions (a smaller upper portion and a larger lower gastric pouch) using an automatic stapling device. The upper pouch typically measures less than about 1 ounce (or 20 cc), while the larger lower pouch remains generally intact and continues to secret stomach juices flowing through the intestinal track.

A segment of the small intestine is then brought from the lower abdomen and joined with the upper pouch to form an anastomosis created through a half-inch opening, also called the stoma. This segment of the small intestine is called the "Roux loop" and carries the food from the upper pouch to the remainder of the intestines, where the food is digested. The remaining lower pouch and the attached segment of duodenum are then reconnected to form another anastomotic connection to the Roux loop at a location approximately 50 to 150 cm from the stoma, typically using a stapling instrument. It is at this connection that the digestive juices from the bypass stomach, pancreas, and liver, enter the jejunum and ileum to aide in the digestion of food. Due to the small size of the upper pouch, patients are forced to eat at a slower rate and are satiated much more quickly. This results in a reduction in caloric intake.

As those skilled in the art will certainly appreciate, the conventional RYGB procedure requires a great deal of operative time. Because of the degree of invasiveness, post-operative recovery time can be quite lengthy and painful. In view of the highly invasive nature relating to the current RYGB procedure, other less invasive procedures have been developed. With this mind other procedures for reducing the size of the stomach have been developed. The most common form of gastric reduction surgery involves the application of vertical staples along the stomach to create an appropriate pouch. This procedure is commonly performed laparoscopically and as such requires substantial preoperative, operative, postoperative resources.

As endoscopic devices and procedures have developed, surgeons have begun to employ endoscopic techniques to gastric procedures such as those discussed above in an effort to minimize trauma and reduce the time required for procedures and recovery. With the foregoing in mind, procedures and apparatuses that allow for the performance of gastric reduction surgery in a time efficient and patient friendly manner are needed.

One area that has not been adequately addressed is the need for the application of sutures as these gastric, and other endoscopic, procedures are being performed. The present invention provides an endoscopic suturing device adapted for the continuous application of sutures.

SUMMARY OF THE INVENTION

It is, therefore, an object of the present invention to provide an endoscopic apparatus for the continuous application of a suture. The apparatus includes a suturing body that is shaped and dimensioned for attachment to the distal end of a commercially available endoscope in a manner permitting actuation thereof. The suturing body is composed of a suture housing in which a needle and drive assembly are housed for movement of the needle about a continuous circular path facilitating the application of a suture secured to a distal end of the needle. The drive assembly includes a rocker that moves along the suture housing under the control of a drive cable and a pin, wherein actuation of the drive cable and pin cause the rocker to selectively engage and disengage the needle causing the needle to move about a circular path in a continuous manner.

It is also an object of the present invention to provide an endoscope for the continuous application of a suture. The endoscope includes an endoscope body. The endoscope also includes a suturing body that is shaped and dimensioned for attachment to the distal end of the endoscope body in a manner permitting actuation thereof. The suturing body is composed of a suture housing in which a needle and drive assembly are housed for movement of the needle about a continuous circular path facilitating the application of a suture secured to a distal end of the needle. The drive assembly includes a rocker that moves along the suture housing under the control of a drive cable and a pin, wherein actuation of the drive cable and pin cause the rocker to selectively engage and disengage the needle causing the needle to move about a circular path in a continuous manner.

It is another object of the present invention to provide an endoscopic apparatus for the continuous application of a suture. The apparatus includes a suturing body that is shaped and dimensioned for attachment to the distal end of a commercially available endoscope in a manner permitting actuation thereof. The suturing body is composed of a suture housing in which a needle and drive assembly are housed for movement of the needle about a continuous circular path facilitating the application of a suture secured to a distal end of the needle. The drive assembly applies axial motion to cause movement of the needle about a continuous circular path.

Other objects and advantages of the present invention will become apparent from the following detailed description when viewed in conjunction with the accompanying drawings, which set forth certain embodiments of the invention.

DESCRIPTION OF THE PREFERRED EMBODIMENT

The detailed embodiment of the present invention is disclosed herein. It should be understood, however, that the disclosed embodiment is merely exemplary of the invention, which may be embodied in various forms. Therefore, the details disclosed herein are not to be interpreted as limiting, but merely as the basis for the claims and as a basis for teaching one skilled in the art how to make and/or use the invention.

With reference to FIGS. 1 to 10, an endoscopic apparatus 10 for the continuous application of a suture 12 is disclosed. Although the apparatus is particularly adapted for use in performing endoscopic gastric reduction procedures, those skilled in the art will certainly appreciate that the device may be used for a wide variety of applications without departing from the spirit of the present invention.

Figure 1:
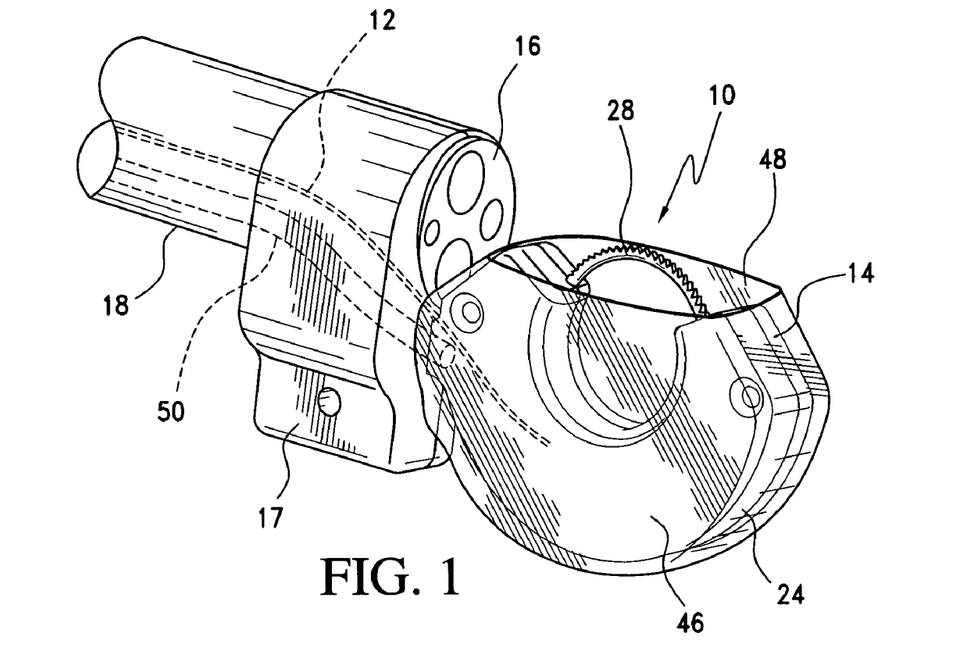
FIG. 1 is a perspective view of the present invention with the vacuum housing secured thereto.
Figure 2:
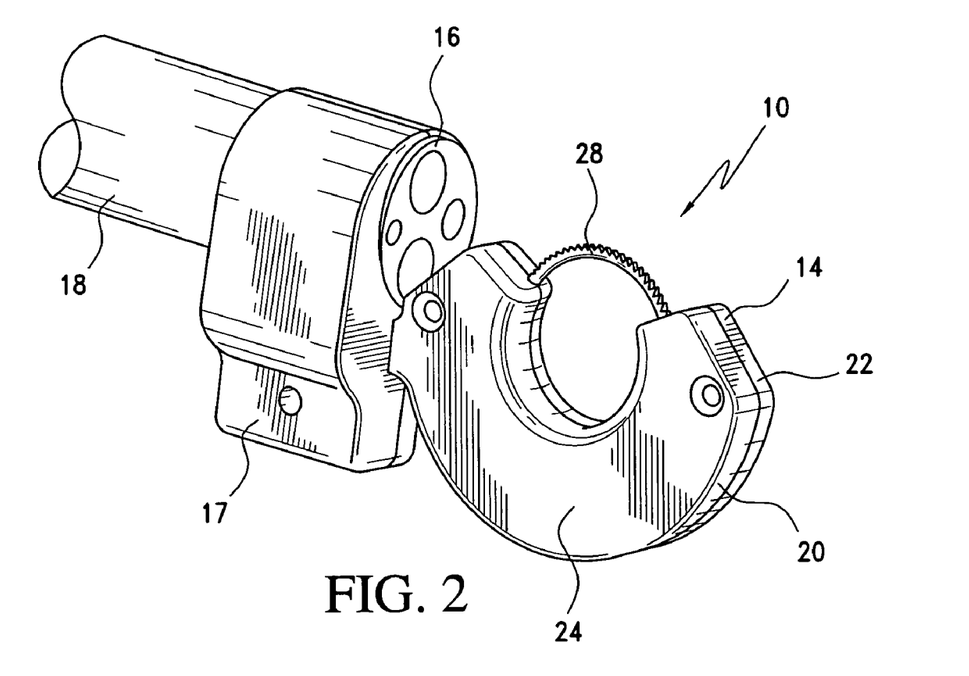
FIG. 2 is a perspective view of the present invention without the vacuum housing.
Figure 3:
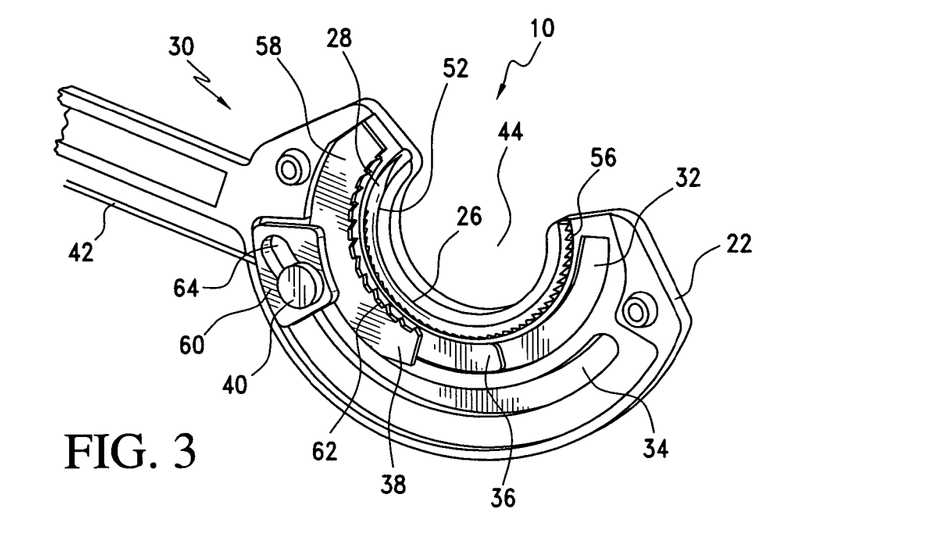
FIGS. 3 through 10 are sectional perspective views demonstrating operation of the present invention.
Figure 4:
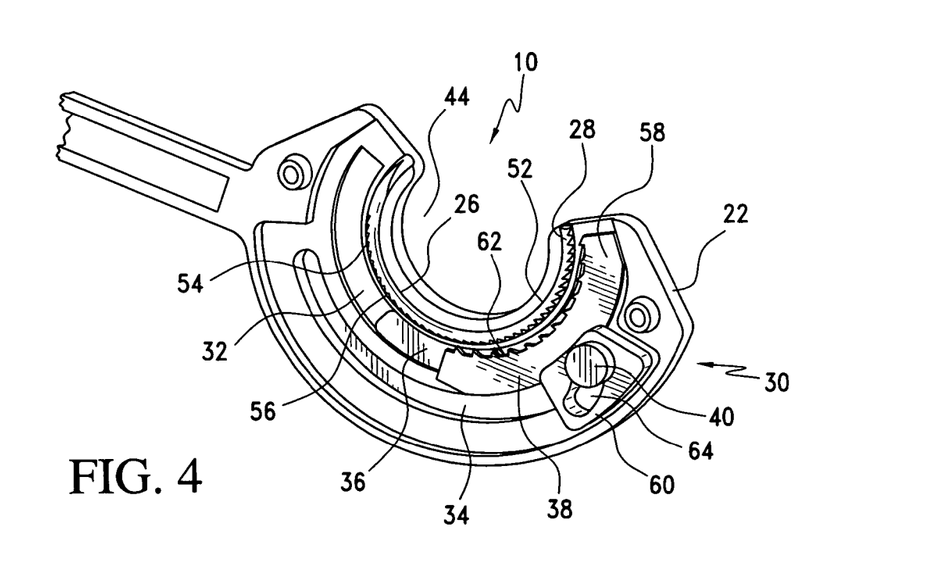
Figure 5:
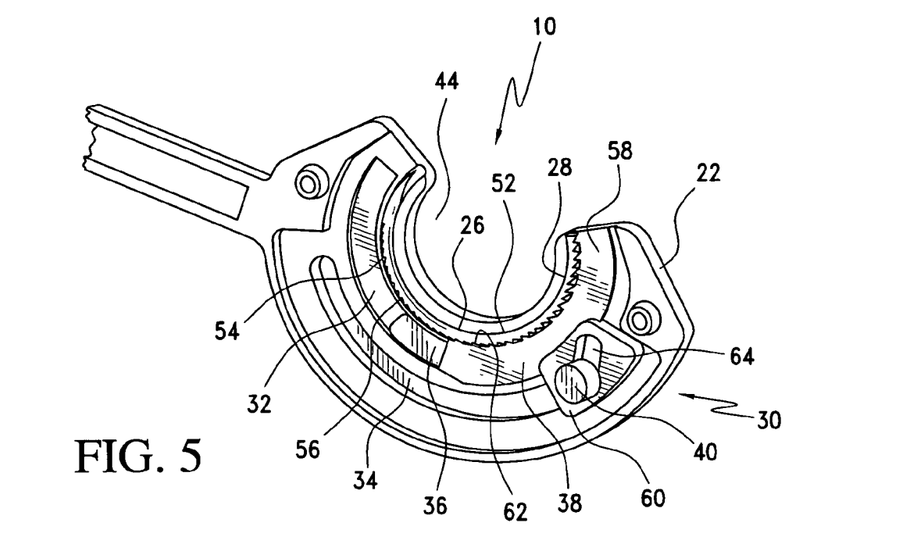
Figure 6:
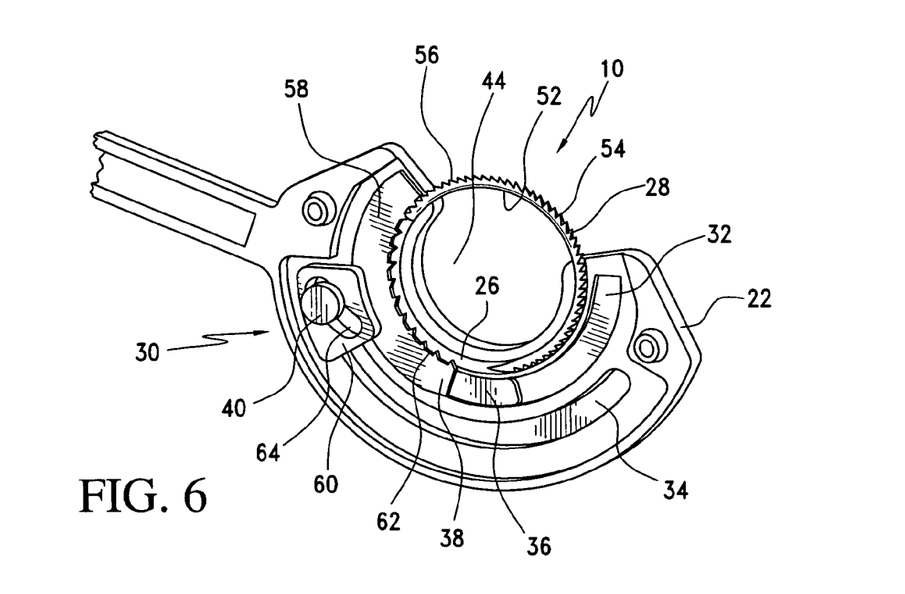
Figure 7:
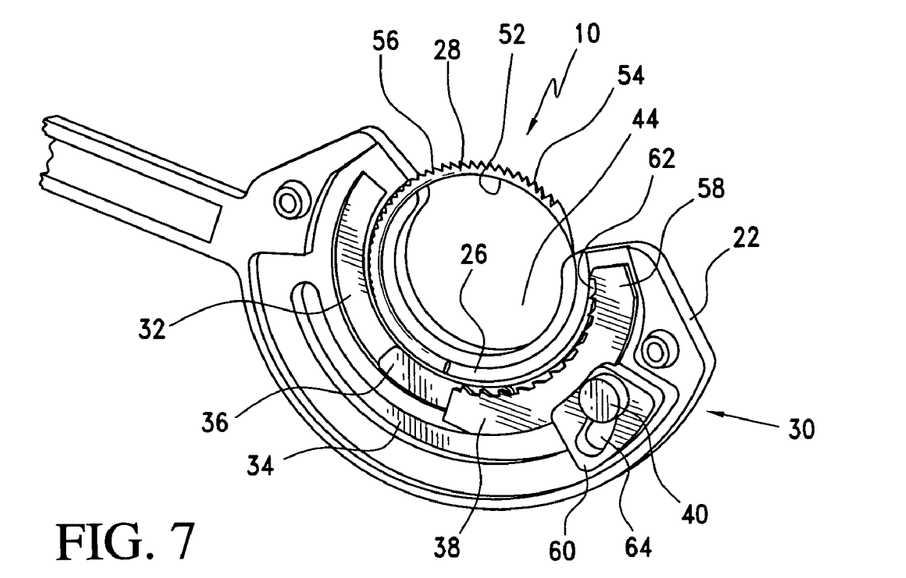
Figure 8:
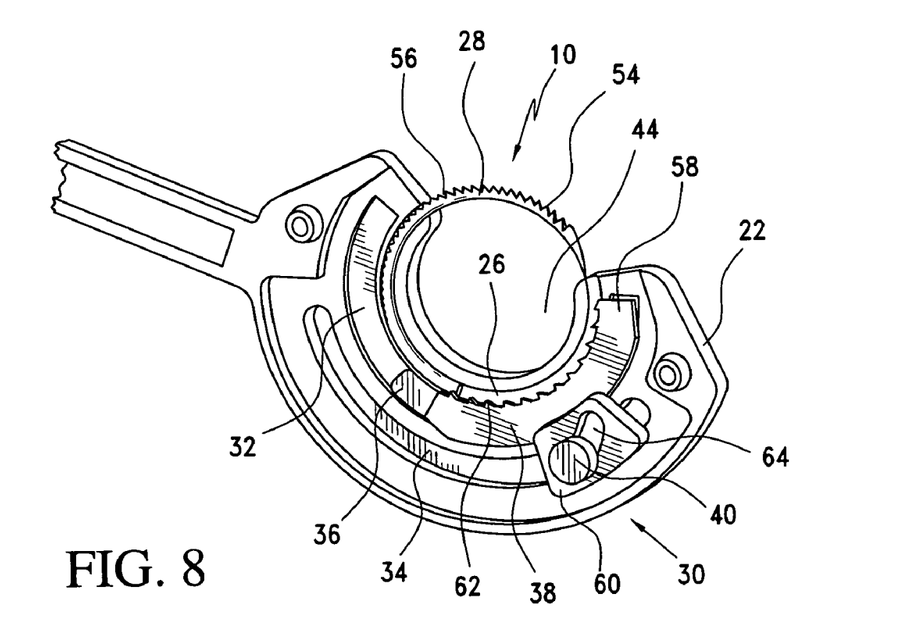
Figure 9:
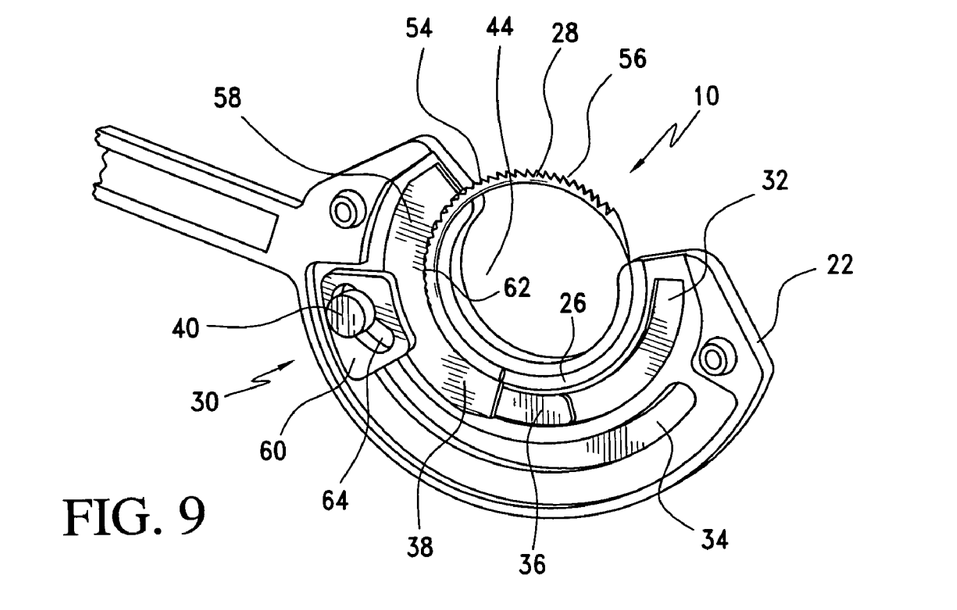
Figure 10:
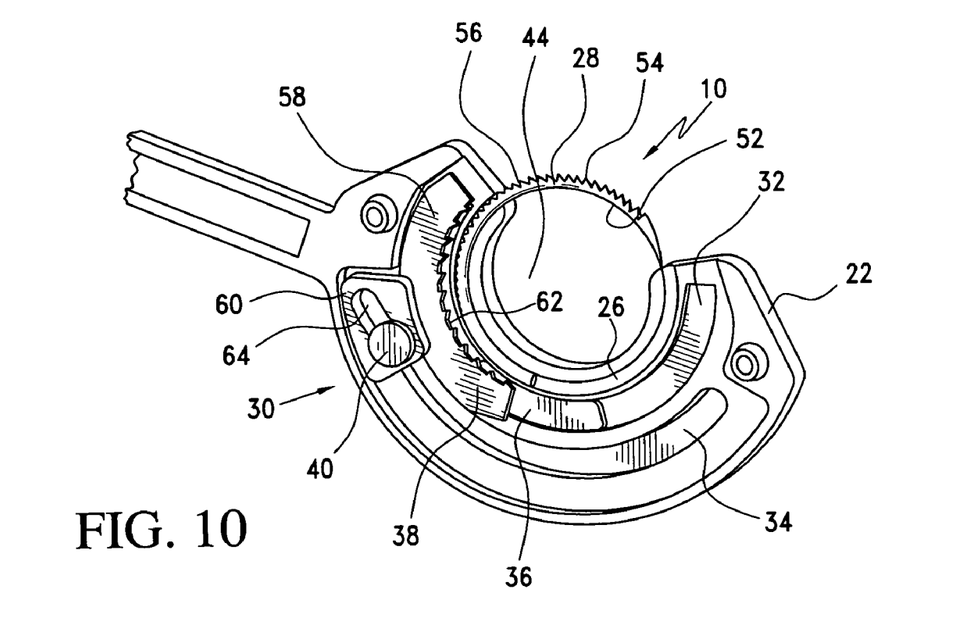

The apparatus 10 includes a suturing body 14 that is shaped and dimensioned for attachment to the distal end 16 of a commercially available endoscope 18 in a manner permitting actuation thereof and the creation of a vacuum. With this in mind, the suturing body 14 is secured to the endoscope 18 using known attachment structures appreciated by those skilled in the art.

The suturing body 14 is composed of a first housing member 20 and a second housing member 22 secured together to creating a housing 24 in which the functional components of the present apparatus 10 are housed for movement in accordance with the present invention. With this in mind, the housing 24 includes an inner first track 26 in which the needle 28 is positioned for movement about a predetermined circular path under the control of the drive assembly 30.

The drive assembly 30 is supported within second and third tracks 32, 34 positioned about the inner first track 26. The drive assembly 30 applies axial motion to cause movement of the needle 28 about a continuous circular path. The drive assembly 30 is generally composed of a friction plate 36 statically mounted along the second track 32 and a rocker 38 that moves along the second track 32 while a pin 40 moves along the outer third track 34. A drive cable 42 is coupled to the pin 40 for controlling actuation thereof in the manner described below in greater detail.

For reasons that will become apparent based upon the operation of the present suture apparatus 10 as described below in greater detail, the suturing body 14 is substantially C-shaped with a central opening 44 in which tissue is positioned during suturing. The C-shape of the suturing body 14 allows the needle 28 to move about a circular path during operation thereof.

Referring to FIGS. 1 and 2, the present endoscopic suture apparatus 10 is attached to commercially available endoscopes 18 by way of a clamp 17. As mentioned above, the suture apparatus 10 may be secured to the endoscope 18 in a variety of ways without departing from the spirit of the present invention. The suture apparatus 10 is oriented in a way that allows the user to maintain visibility of the needle 25 and operative field, as well as create a small cross section to aid in transoral insertion (when the apparatus is used in gastric surgical procedures).

A vacuum housing 46 surrounds the suturing body 14 of the present suture apparatus 10 defining a cavity 48 in which the suturing body 14 sits. The vacuum housing 46 is coupled to the vacuum line 50 of the endoscope 18 such that a vacuum is created within the cavity 48 defined by vacuum housing 46, as well as the central opening 44 of the suturing body 14. In this way, the application of the vacuum draws adjacent tissue into the central opening 44 of the suturing body 14.

As mentioned above, the housing 24 contains a needle 28 used in the application of a suture 12 to the tissue drawn within the central opening 44. The suture 12 is secured to the distal end of the needle 28 and is drawn through the tissue as the needle 28 is actuated in accordance with the present invention as described herein. The needle 28 is curved to rotate about a predetermined circular path. The needle 28 extends along an arc of 240 degrees creating an opening of 120 degrees. However, those skilled in the art will appreciate that the opening may be varied; for example, we have contemplated use of a needle offering an opening of 140 degrees. The needle 28 includes an interior surface 52 along the inner surface of the arc defined by the needle 28 and an exterior surface 54 along the outer surface of the arc defined by the needle 28. A series of notches 56 are cut into the exterior surface 54 of the needle 28. As will be appreciated based upon the following description, the notches 56 are shaped and dimensioned for used by the drive assembly 30 in grabbing, driving and releasing the needle 28. Although notches along the exterior surface of the needle are disclosed for use in accordance with a preferred embodiment of the present invention, it is contemplated the needle may be formed without notches such that the drive assembly merely grips the substantially smooth exterior surface of the needle to drive it forward.

Operation of the drive assembly 30 and movement of the needle 28 is described with reference to FIGS. 3 to 10, wherein one half of the housing 24 is removed, exposing internal components of the present suture apparatus 10. The drive cable 42 is rigidly attached to the pin 40. As is described below in greater detail, the drive cable 42, pin 40 and rocker 38 are extended and retracted to engage and disengage the needle 28 for movement thereof about its circular path. The drive cable 42 is flexible enough to curve in the housing 24 and flex along with the endoscope 18, but is rigid enough to be compressed to drive the rocker 38 into its initial drive stage (see FIG. 4).

The rocker 38 is composed of an arcuate engagement member 58 and a camming member 60 working in conjunction with the pin 40 to control the position of the engagement member 58 for selective engagement with the needle 28. The engagement member 58 is constructed with internal notches 62 shaped and dimensioned for engaging the needle 28 to drive it in a clockwise direction, but permit free movement thereof as the rocker 38, that is, both the engagement member 58 and the camming member 60, is moved in a counterclockwise direction toward the initial drive stage.

The engagement member 58 of the rocker 38 is designed to translate in the housing 24 both radially towards and away from the needle 28, as well as translate arcuately clockwise and counterclockwise about the arc defined by the housing 24. This is achieved through the camming action offered by the interaction between the camming member 60, the pin 40 and the engagement member 58. The camming member 60 is rigidly coupled to the engagement member 58 such that the engagement member 58 is moved into and out of engagement with the needle 28 as the radial position of the camming member 60 is altered based upon its interaction with the pin 40. It is also contemplated that a spring element may be employed to force the rocker element 38 against the needle 28.

More particularly, as the drive cable 42 is compressed (that is, pressed forward) to move the rocker 38 in a counter-clockwise direction, the pin 40 slides within a slot 64 formed in the camming member 60 forcing the engagement member 58 and camming member 60 to move counterclockwise as well as outwardly from the needle 28. The friction plate 36 aids in forcing the engagement member 58 outwardly from the needle 28 as the rocker 38 is moved in this counter-clockwise direction.

As tension is applied to the drive cable 42 and ultimately the pin 40, the pin 40 slides within the camming member 60 applying pressure to the engagement member 58 and camming member 60 which causes the engagement member 58 and camming member 60 to travel inwardly into contact with the exterior surface 54 of the needle 28 due to the camming action resulting from the interaction of the pin 40 and the slot 64 within the camming member 60. As tension is continually applied to the drive cable 42 the notches 62 formed along the inner surface of the engagement member 58 grab into the notches 56 cut into the exterior surface 54 of the needle 28, causing the needle 28 to rotate clockwise until the rocker 38 runs into the housing 24 and the procedure must start all over.

As the limit of the stroke is reached, the operator compresses the drive cable 42 causing the engagement member 58 to disengage from the needle 28 by way of the cam feature resulting from the interaction of the pin 40 within the slot 64 of the camming member 60 as the pin 40 slides within the slot 64 causing the engagement member 58 and camming member 60 to move outwardly and in a counterclockwise direction. The compression on the drive cable 42 is continued until the rocker 38 moves counterclockwise reaching the opposite end of the housing 24. Tension is then applied to once again move the needle 28 in a clockwise direction and the procedure is repeated until the needle has traveled 360 degrees.

While the preferred embodiments have been shown and described, it will be understood that there is no intent to limit the invention by such disclosure, but rather, is intended to cover all modifications and alternate constructions falling within the spirit and scope of the invention.

The invention claimed is:

1. An endoscopic apparatus for the continuous application of a suture, comprising:
a suturing body that is shaped and dimensioned for attachment to the distal end of a commercially available endoscope in a manner permitting actuation thereof;
the suturing body is composed of a suture housing in which a needle and drive assembly are housed for movement of the needle about a continuous circular path facilitating the application of a suture secured to a distal end of the needle, the suture housing including a first track in which the needle is positioned, a second track and a third track;
the drive assembly includes a rocker that moves along the second track of the suture housing under the control of a drive cable and a pin that moves along the third track of the suture housing, wherein actuation of the drive cable and pin cause the rocker to selectively engage and disengage the needle causing the needle to move about a circular path in a continuous manner.

2. An endoscopic apparatus according to claim 1, wherein a vacuum housing surrounds the suturing body, the vacuum housing being shaped and dimensioned for coupling to a vacuum line of the endoscope.

3. An endoscopic apparatus according to claim 1, wherein the needle is arcuate.

4. An endoscopic apparatus according to claim 1, wherein the needle includes an interior surface, an exterior surface, and a notch formed along the exterior surface of the needle, and the rocker includes a notch shaped and dimensioned for engaging the notch along the exterior surface of the needle during actuation thereof.

5. An endoscopic apparatus according to claim 1, wherein the rocker is composed of an engagement member and a camming member working in conjunction with the pin to control the position of the engagement member for selective engagement with the needle.

6. An endoscopic apparatus according to claim 5, wherein the camming member includes a slot in which the pin moves for causing the engagement member to move into and out of engagement with the needle.

7. An endoscopic apparatus according to claim 5, wherein the rocker further includes a friction plate which aids in controlling the positioning of the engagement member.

8. An endoscopic apparatus according to claim 5, wherein the engagement member is arcuate to substantially conform to the shape of the needle.

9. An endoscope for the continuous application of a suture, comprising:
an endoscope body;
a suturing body that is shaped and dimensioned for attachment to the distal end of the endoscope body in a manner permitting actuation thereof;
the suturing body is composed of a suture housing in which a needle and drive assembly are housed for movement of the needle about a continuous circular path facilitating the application of a suture secured to a distal end of the needle, the suture housing including a first track in which the needle is mounted, a second track and a third track;
the drive assembly includes a rocker that moves along the second track of the suture housing under the control of a drive cable and a pin that moves along the third track of the suture housing, wherein actuation of the drive cable and pin cause the rocker to selectively engage and disengage the needle causing the needle to move about a circular path in a continuous manner.

10. An endoscope according to claim 9, wherein a vacuum housing surrounds the suturing body, the vacuum housing being coupled to a vacuum line of the endoscope.

11. An endoscope according to claim 9, wherein the needle is arcuate.

12. An endoscope according to claim 9, wherein the needle includes an interior surface and an exterior surface, and a s notch formed along the exterior surface of the needle, and the rocker includes a notch shaped and dimensioned for engaging the notch along the exterior surface of the needle during actuation thereof.

13. An endoscope according to claim 9, wherein the rocker is composed of an engagement member and a camming member working in conjunction with the pin to control the position of the engagement member for selective engagement with the needle.

14. An endoscope according to claim 13, wherein the camming member includes a slot in which the pin moves for causing the engagement member to move into and out of engagement with the needle.

15. An endoscope according to claim 13, wherein the rocker further includes a friction plate which aids in controlling the positioning of the engagement member.

16. An endoscope according to claim 13, wherein the engagement member is arcuate to substantially conform to the shape of the needle.

* * * * *

UNITED STATES PATENT AND TRADEMARK OFFICE
CERTIFICATE OF CORRECTION

PATENT NO.      : 7,615,060 B2                          Page 1 of 1
APPLICATION NO. : 11/150481
DATED           : November 10, 2009
INVENTOR(S)     : Stokes et al.

It is certified that error appears in the above-identified patent and that said Letters Patent is hereby corrected as shown below:

On the title page,

Item [*] Notice:   Subject to any disclaimer, the term of this patent is extended or adjusted under 35 USC 154(b) by 732 days Delete the phrase "by 732 days" and insert -- by 1,183 days --

Signed and Sealed this

Twentieth Day of April, 2010

David J. Kappos
*Director of the United States Patent and Trademark Office*